(12) United States Patent
Scheiwe et al.

(10) Patent No.: US 6,492,395 B1
(45) Date of Patent: Dec. 10, 2002

(54) TOPICAL FORMULATION OF ALKYL-, PHENYL-PYRIDONE

(75) Inventors: Max Werner Scheiwe, Maulburg (DE); Shitotomo Yamauchi, Tokyo (JP)

(73) Assignee: Mepha AG, Aesch (CH)

( * ) Notice: Subject to any disclaimer, the term of this patent is extended or adjusted under 35 U.S.C. 154(b) by 0 days.

(21) Appl. No.: 09/787,474

(22) PCT Filed: Sep. 18, 1998

(86) PCT No.: PCT/EP98/05971

§ 371 (c)(1),
(2), (4) Date: May 23, 2001

(87) PCT Pub. No.: WO00/16775

PCT Pub. Date: Mar. 30, 2000

(51) Int. Cl.⁷ ............................................. A61K 31/445
(52) U.S. Cl. ....................................................... 514/327
(58) Field of Search ......................................... 514/327

(56) References Cited

U.S. PATENT DOCUMENTS

| | | | |
|---|---|---|---|
| 4,052,509 A | * | 10/1977 | Gadekar et al. |
| 4,185,106 A | * | 1/1980 | Dittmer et al. |
| 4,762,847 A | * | 8/1988 | Edwards et al. |
| 5,310,562 A | | 5/1994 | Margolin |
| 5,468,492 A | * | 11/1995 | Szaliki et al. |
| 5,518,729 A | | 5/1996 | Margolin |
| 5,716,632 A | | 2/1998 | Margolin |
| 5,766,579 A | * | 6/1998 | Earles |
| 6,090,822 A | * | 7/2000 | Margoline |

FOREIGN PATENT DOCUMENTS

| | | |
|---|---|---|
| EP | 0 383 591 | 8/1980 |
| WO | WO 94/26249 | 11/1994 |
| WO | WO 97/41830 | 11/1997 |

* cited by examiner

*Primary Examiner*—William R. A. Jarvis
*Assistant Examiner*—Vickie Kim
(74) *Attorney, Agent, or Firm*—Hoffmann & Baron, LLP

(57) ABSTRACT

A pharmaceutically acceptable topical formulation for the treatment and/or prevention of skin ailments, more particularly of fibriotic nature such as fibriotic lesional tissues, contiguous warts, contact dermatitis, and keloids, and to assist the healing of burns after surgery, comprising as active ingredient a substituted pyridone of the formula: n-($R^1$)-$R^2$-2-(1H)pyridone or a pharmaceutically acceptable salt or ester thereof, where $R^1$ is selected from methyl, ethyl, propyl, carboxyl and a carboxymethyl or carboxyethyl ester group, $R^2$ is selected from phenyl, methylphenyl, ethylphenyl, propylphenyl, and a carboxyphenyl or carboxyethylphenyl ester group, and n is 3, 4 or 5, together with an excipient, characterized in that the excipient comprises, one or more plasticisers, one or more antioxidants, one or more gel-forming agents and sufficient pH adjusting agent to bring the pH of the formulation to a value from 4 to 8. The preferred active ingredient is 5-methyl-1-phenyl-2-(1H) pyridone (Pirfenidone).

20 Claims, No Drawings

TOPICAL FORMULATION OF ALKYL-, PHENYL-PYRIDONE

BACKGROUND OF THE INVENTION

The present invention relates to topical formulations, e.g. creams, ointments, gels and the like containing as active ingredient one or more alkyl, phenyl pyridones, more particularly a substituted pyridone of the formula:

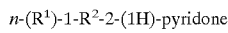
n-(R¹)-1-R²-2-(1H)-pyridone or a pharmaceutically acceptable salt or ester thereof, where $R^1$ is selected from methyl, ethyl, propyl, carboxyl and a carboxymethyl or carboxyethyl ester group, $R^2$ is selected from phenyl, methylphenyl, ethylphenyl, propylphenyl, and a carboxyphenyl or carboxyethylphenyl ester group, and n is 3, 4 or 5 (position of substitution). The preferred active ingredient is Pirfenidone (CAS 53179-13-8, 5-methyl-1-phenyl-2-(1H)-pyridone).

As described in U.S. Pat. No. 5,310,562 and EP 0 383 591, Pirfenidone has a broad spectrum of applications in the prevention and treatment of fibrotic diseases, especially for the reparation and prevention of fibrotic lesional tissues, contiguous warts, contact dermatitis, keloids, fibrosis of the lung, fibrosis of the prostate, sclerosis, the healing of burns after surgery and Alzheimer disease. Although the possibility of topical application is mentioned, there is no description of any specific formulation.

The application of active ingredients of the class mentioned, (hereafter called alkyl,phenyl pyridones) e.g. Pirfenidone for e.g. the treatment of burns and keloids may possibly be carried out using a solution or a suspension of the agent in aqueous or oily excipient such as emulsions, creams, ointments, gels, microemulsions, liquid emulsions, nanocapsule suspensions, liposome formulations, lotions and the like; however, an ointment, cream or gel formulation is preferable because of their soothing effect and easy application. Because these formulations are used in the treatment of humans they are considered to be pharmaceutical preparations, and as thus have to be proven to be physically and chemically stable before they are permitted on the market. For this reason, each formulation must undergo a stability test. Without the necessary data on stability and shelf life, the formulation cannot be approved by any health authority.

Typical parameters for stability include homogeneity of the formulation in all parts of its volume, absence of coalescence of emulsion droplets, practically constant viscosity, a semi-solid structure, complete dissolution of the active ingredient, and absence of recrystallisation of the active ingredient. Also, the formulation should be prepared using pharmaceutically acceptable excipients, preferably described in pharmacopoeias, otherwise the acceptability of the excipients must be proven separately in costly programs that comprise among others a complete toxicology investigation or other means that show safety, tolerance and efficacy for the intended medicinal treatment.

It was found that standard excipient preparations e.g. as described in the USP (United States Pharmacopoeia) are unsuitable for use in the preparation of pharmaceutically acceptable topical formulations such as ointments containing a sufficient dosage of the active ingredient. The preparations lack physical stability. It was found that 5-methyl-1-phenyl-2-(1H)-pyridone is a so called emulsion destabiliser, i.e. tends to destabilise physically emulsions and other colloidal systems.

SUMMARY OF THE INVENTION

The main object of the present invention is to provide a pharmaceutically acceptable topical formulation with an excipient which permits the dissolution or dispersion of a sufficient amount of Pirfenidone (or like pharmaceutically acceptable alkyl,phenyl pyridone or salt or ester thereof) to be useful for medical treatment, and that at the same time provides the formulation with sufficient stability and shelf life.

The invention provides a pharmaceutically acceptable topical formulation for the treatment and/or prevention of skin ailments, more particularly of fibrotic nature such as fibrotic lesional tissues, contiguous warts, contact dermatitis, and keloids, and to assist the healing of burns after surgery, comprising as active ingredient a substituted pyridone of the formula:

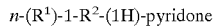
n-(R¹)-1-R²-(1H)-pyridone or a pharmaceutically acceptable salt or ester thereof, where $R^1$ is selected from methyl, ethyl, propyl, carboxyl and a carboxymethyl or carboxyethyl ester group, $R^2$ is selected from phenyl, methylphenyl, ethylphenyl, propylphenyl, and a carboxyphenyl or carboxyethylphenyl ester group, and n is 3, 4 or 5, together with an excipient, characterised in that the excipient comprises one or more plasticisers, one or more antioxidants, one or more gel-forming agents and sufficient pH adjusting agent to bring the pH of the formulation to a value from 4 to 8. Preferably the pH of the formulation is from about 5 to about 7.5.

The preferred active ingredient is 5-methyl-1-phenyl-2-(1H)-pyridone (Pirfenidone), or a pharmaceutically acceptable salt or ester thereof. The concentration of said active ingredient is preferably within the range of about 0.5% (by weight) to about 9% (weight), preferably from about 3% (by weight) to about 7% (by weight) calculated to the weight of the entire composition.

As plasticiser it is preferred to use one or more alkyl glycols and polyalkylene glycols, e.g. polyethylene glycol and/or polypropylene glycol. Other possible plasticisers include benzyl benzoate, chlorobutanol, mineral oil, (CTFA mixture of mineral oils, e.g. Amerchol L-101, Protalan M-16, Protalan M-26), petrolatum (CTFA, mixture of petrolatum, e.g. Amerchol CAB, Forlan 200), and lanolin alcohols, sorbitol, triacetin, dibutyl sebacate, diethyl phthalate, glycerine, petrolactam and triethyl citrate.

As antioxidant it is preferred to use sodium metabisulfite. Other possible antioxidants include alphatocopherol, ascorbic acid, malic acid, sodium ascorbate, ascorbyl palmitate, butylated hydroxyanisole, butylated hydroxytoluene, fumaric or maleic acid, and propyl gallate.

As a gel-forming agent it is preferred to use a carboxypolyalkylene, especially Carbomer (carboxypolymethylene, CAS 541823-57-9) of which different grades with various molecular weights are commercially available. Other possible gel-forming agents include cetostearyl alcohol, colloidal silicon dioxide, gelatine, guar gum, sodium or calcium carboxymethyl cellulose, hydroxyethyl or hydroxypropyl cellulose, hydroxypropylmethylcellulose, methyl or ethyl cellulose, maltodextrin, polyvinyl alcohol, propylene carbonate, povidone, propylene glycol alginate, alginic acid sodium alginate, sodium starch glycolate, starch, sucrose.

The gel-forming agents can be included with emulsifying agents or gums such as acacia gum, guar gum, tragacanth, xanthan gum and fillers or thickening agents such as bentonite and magnesium aluminium silicate.

Preferred emulsifying agents are acacia, anionic emulsifying wax, cetostearyl alcohol, cetyl alcohol, cholesterol, diethanolamine, glyceryl monostearate, hydrous lanolin, lanolin, lanolin alcohols, lecithin, monobasic sodium phosphate, monoethanolamin, nonionic emulsifying wachs, oleic acid, poloxamer, polyoxyethylene alkyl ethers, polyoxyethylene castor oil derivatives, polyoxyethylene sorbiaten fatty acid esters, polyoxyethylene stearates, propylene glycol alginates, sodium lauryl sulfates, sorbitan esters, stearic acid, triethanolamine.

Antimicrobial agents such as benzyl benzoate may be included. Preferred antimicrobial agents are also benzalkonium chloride, benzethonium chloride, benzoic acid, benzyl alcohol, butylparaben, ethylparaben, methylparaben, propylparaben, cetrimide, chlorhexidine, chlorobutanol, chlorocresol, cresol, glycerin, imidurea, phenol, phenoxyethanol, phenylethylalcohol, phenylmercuric acetate, phenylmercuric borate, phenylmercuric nitrate, potassium sorbate, sodium benzoate, sodium proprionate, sorbic acid, thiomersal.

Although purified water, preferably de-ionised, is used as the main vehicle, one or more alcohols may be included, such as ethanol and/or isopropanol.

Methylparaben and/or Propylparaben may be included. For the adjustment of the pH is preferred to use alkali hydroxide, e.g. sodium hydroxide.

A typical formulation and typical ratios (in % by weight calculated to the weight of the entire composition) according to the invention comprises:

| active ingredient | 3 to 7 wt. % |
|---|---|
| plasticiser | 5 to 65 wt. % |
| antioxidant | 0.02 to 2 wt. % |
| gel-forming agent | 0.5 to 5 wt. % |
| pH adjusting agent | 0.2% to 5 wt. % |
| one or more alcohols | 0 to 20 wt. % |
| purified water | 20% to 80 wt. %. |

A preferred formulation comprises:

| active ingredient | 3 to 7 wt. % |
|---|---|
| polypropyleneglycol | 5 to 65 wt. % |
| sodium metabisulfite | 0.02 to 2 wt. % |
| carboxypolymethylene | 0.5 to 5 wt. % |
| NaOH (5N) | 0.2 to 5 wt. % |
| Methylparaben and/or Propylparaben | 0 to 0.5 wt. % |
| ethanol and/or propanol | 0 to 20 wt. % |
| purified water | 20% to 80 wt. %. |

The pH is preferably adjusted to a value from 5.2 to 6.6.

The preferred formulations according to the invention result in an cosmetically acceptable clear gel of sufficient viscosity to form a semisolid which shows no phase separation or crystallisation effects with Pirfenidone as the active ingredient, neither initially after manufacture nor after 3 or 6 months or more prolonged storage at room temperature. For application to skin having open wounds, a gel formulation according to the invention without ethanol or isopropanol is also possible and useful; this is desirable because these alcohols can cause pain in such wounds.

The following Comparative Examples illustrate topical formulations with a sufficient dosage of Pirfenidone using standard excipient materials.

COMPARATIVE EXAMPLE 1

Hydrophilic ointment according to USP 23 (United States Pharmacopoeia)

The excipient materials of this formulation are given as follows:

| polypropyleneglycol | 12.0 g |
|---|---|
| stearyl alcohol | 25.0 g |
| white petrolatum | 25.0 g |
| Methylparaben | 0.025 g |
| Propylparaben | 0.015 g |
| sodium lauryl sulfate | 10.0 g |
| purified water | 27.9 g |

In this ointment base, Pirfenidone was incorporated using the following conventional technique as described in USP 23 in concentrations of 3.5; 5.0 and 10% (wt/wt).

Stearyl alcohol and white petrolatum were melted on a steam bath, and warmed to about 75° C. The remaining ingredients were added including Pirfenidone, previously dissolved in water and warmed to 750° C., and the mixture was stirred until it congealed. The finished ointment was then filled into cylindrical small plastic pots, and closed with a screw cap.

A stability test of the preliminary type was successfully carried out, showing the ointment to be initially physically stable, before starting on a full stability test including physicochemical and chemical parameters. After a storage time of 6 months under standard storage conditions (25° C.±2° C., 59% rh±5% ), the ointment preparations developed phase separation effects, the emulsion became inhomogeneous by coalescence effects, and also large crystals built up from the active principle in all concentrations of the active principle used. Part of the ointment was so much lowered in viscosity that it became a practically free flowing liquid.

COMPARATIVE EXAMPLE 2

A hydrophilic ointment or cream was prepared according to the following formulation:

| Pirfenidone | 5.0 g |
|---|---|
| polypropylene glycol | 5.0 g |
| oleic acid decylester | 5.0 g |
| middle chain triglycerides | 10.0 g |
| diisopropyl adipate | 5.0 g |
| stearic acid | 5.0 g |
| cetyl stearyl alcohol | 5.0 g |
| polyoxyethylene-40-stearate | 2.5 g |
| sorbitan monostearate | 2.5 g |
| Methylparaben Sodium | 0.2 g |
| Propylparaben Sodium | 0.2 g |
| purified water | 54.6 g |

The following components: oleic acid decylester, middle chain triglycerides, diisopropyl adipate, stearic acid, cetylstearyl alcohol, polyoxyethylene-40-stearate, and sorbitan monostearate were melted on a steam bath and heated to 80° C. under gentle agitation. The residual components were dissolved in water including the active principle and heated to 80° C. The hot aqueous solution was added under vigorous agitation to the melt, and cooled under agitation to 30° C. The finished ointment was then filled into cylindrical small plastic pots and closed with a screw cap; one part was packaged in tubes.

Stability testing was carried out as above.

The formulation showed normal stability initially; however after 6 months storage under standard storage conditions (25° C.±2° C., 60% rh±5% ) the ointment showed recrystallisation of the active principle. When applied to the skin small sharp grains of the active ingredient caused unacceptable scratching. Because of this effect, the formulation had to be rejected for presentation to health authorities for approval. At the same time, no alteration in assay of Pirfenidone in this formulation occurred.

COMPARATIVE EXAMPLE 3

A gel was prepared according to the following formulation:

| | |
|---|---|
| Pirfenidone | 5.0 g |
| Polypropylene glycol | 20.0 g |
| ethanol 96% | 28.0 g |
| hydroxyethyl cellulose | 1.25 g |
| purified water | 45.75 g |

The polypropylene glycol and water were mixed to a nearly clear solution into which the Pirfenidone was completely dissolved. The hydroxyethyl cellulose was then added slowly under stirring and the product homogenised. Tubes were filled with the formulation.

Stability testing was carried out as above.

The product was initially a clear, smooth homogeneous, colourless gel having a pH of 6.2 (potentiometric measurement), and a viscosity of 2230 mPa.s (shear stress 41.7/s, at 250° C.).

Although initially the gel had good cosmetic properties, after 6 months storage (25° C.±2° C., 60% rh±5%), crystallisation of the active ingredient occurred. Thus, this formulation also showed insufficient stability and could not be regarded as a pharmaceutically acceptable preparation.

COMPARATIVE EXAMPLE 4

A gel was prepared according to the following formulation:

| | |
|---|---|
| Pirfenidone | 3.5 g |
| polypropylene glycol | 21.5 g |
| Isopropanol | 28.0 g |
| Diisopropyl adipate | 2.75 g |
| hydroxypropyl cellulose | 1.25 g |
| purified water | 43.00 g |

The polypropylene glycol, isopropanol and water were mixed to a clear solution and the Pirfenidone dissolved completely in it. The hydroxypropyl cellulose, and diisopropyl adipate were added under stirring and the product homogenised.

Tubes were filled with the formulation.

Although the initial product was homogeneous and colourless it was not clear. It had a pH of 6.3 (potentiometric measurement), a viscosity of 1910 mPa.s (shear stress 41.7/s at 25° C.). Since this formulation was not clear, it was unacceptable as a pharmaceutical preparation.

The following examples illustrate the invention.

EXAMPLE 1

A formulation was prepared as follows:

| | |
|---|---|
| Pirfenidone | 7.0 g |
| polypropylene glycol | 47.5 g |
| Carbomer | 1.5 g |
| sodium metabisulfite | 0.20 g |
| 5N NaOH | 2.20 g |
| purified water | 41.6 g |

The polypropylene glycol and some of the water were mixed and the Pirfenidone added and mixed until a clear solution was obtained. The sodium metabisulfite was dissolved in more water and added. The Carbomer was then added in portions to the mix and the whole mixed to homogeneity. 5-Normal sodium hydroxide solution was added until a pH of 5.5 was reached and the product homogenised.

The formulation was then assayed for content of active ingredient and the presence of degradation products as well as for pH and viscosity. Tubes were then filled with the product.

A clear, viscous, homogeneous gel resulted which applied smoothly to the skin.

The final analytical results were as follows:

| | |
|---|---|
| Aspect | transparent, clear, of minimal yellow colour, no crystallisation |
| pH (potentiometric) | 6.1 |
| Viscosity | 3480 mPa · s |

(rotation-type viscometer, shear rate 41.7/s, at 29° C.)

Content of active principle (HPLC) 98.3% of theoretical value

Content of impurities and degradation products<0.1% (HPLC, 100% method)

Stability test results:Initially, a clear gel was obtained; after 6 months storage (25° C.±2° C., 60% rh±5%, 31° C.±20° C., 70% rh) no crystallisation of the active ingredient was apparent. The pH, viscosity, assay and degradation products did not show larger deviations than are to be expected due to the method of analysis. Thus, this formulation proved to be stable and could be regarded as a pharmaceutically acceptable preparation.

EXAMPLE 2

The formulation was prepared as follows:

| | |
|---|---|
| Pirfenidone | 5.0 g |
| polypropylene glycol | 47.28 g |
| sodium metabisulfite | 0.20 g |
| Carbomer | 1.50 g |
| 5N NaOH | 2.20 g |
| Methylparaben | 0.20 g |
| Propylparaben | 0.024 g |
| purified water | 43.60 g |

The polypropylene glycol was charged to a pharmaceutically acceptable mixer and the Pirfenidone, Methylparaben and Propylparaben added and mixed until a clear solution was obtained. The sodium metabisulfite was dissolved in water and added. The Carbomer was then added in portions and the product homogenised. 5-Normal sodium hydroxide solution was added until a pH of 6.4 was reached and the product further homogenised.

The product was then assayed for content of active ingredient and degradation products as well as pH and viscosity. Tubes were then filled with the formulation. A clear, viscous, homogeneous gel was obtained, which applied smoothly to skin.

The final analytical results were as follows:

| Aspect | transparent, clear, of minimal yellow colour, no crystallisation |
|---|---|
| pH (potentiometric) | 6.4 |
| Viscosity | 3940 mPa · s |

(rotation-type viscometer, shear rate: 41.7/s, at 25° C.):

Content of active principle (HPLC) 101,2% of theoretical value

Content of impurities and degradation products <0.1% (HPLC, 100% percent method)

Stability test results: Initially, a clear gel was obtained; after 6 months storage (25° C.±2° C., 60% rh±5%, 31° C.±2° C., 70% rh), no crystallisation of the active principle was apparent. pH, viscosity, assay and degradation products did not show larger deviations than are to be expected due to the method of analysis. Thus, also this formulation proved to be stable and could be regarded as pharmaceutically acceptable.

EXAMPLE 3

The formulation was prepared as follows:

| Pirfenidone | 3.5 g |
|---|---|
| polypropylene glycol | 16.5 g |
| ethanol (96%) | 10.0 g |
| sodium metabisulfite | 0.20 g |
| Carbomer | 1.50 g |
| N UaOH | 11.50 g |
| purified water | 56.80 g |

The polypropylene glycol and ethanol were charged to a pharmaceutically acceptable mixer and the Pirfenidone added and mixed until a clear solution was obtained. The sodium metabisulfite was then dissolved in water and added. The Carbomer was added in portions and the product homogenised. Normal sodium hydroxide solution was added until a pH of 5.25 was reached and the product further homogenised.

The product was then assayed for content of active ingredient and degradation products as well as for pH and viscosity and finally charged to tubes.

A clear, viscous, homogeneous gel was obtained, which applied smoothly to skin.

The final analytical results were as follows:

| Aspect | transparent, clear, of minimal yellow colour, no crystallisation |
|---|---|
| pH (potentiometric) | 5.25 |
| Viscosity | 3120 mPa · s |

(rotation-type viscometer, shear rate: 41.7/s, at 25° C.)

Content of active principle (HPLC) 99,6% of theoretical value

Content of impurities and degradation products<0.1% (HPLC, 100% percent method).

Stability test results:Initially, a clear gel was obtained; after 6 months storage (25° C.±2° C., 60% rh±5%, 31° C.±2° C., 70% rh), no crystallisation of the active principle was apparent. pH, viscosity, assay and degradation products did not show larger deviations than are to be expected due to the method of analysis. Thus, this formulation proved to be stable and could be regarded as pharmaceutically acceptable.

What is claimed is:

1. A pharmaceutically acceptable topical composition for the treatment and prevention of skin ailments comprising:
   a) an active composition present in an amount of about 3% to about 7% by weight of said topical composition comprising a substituted pyridone corresponding to the formula:

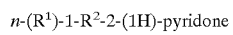

$n$-($R^1$)-1-$R^2$-2-(1H)-pyridone or a pharmaceutically acceptable salt or ester thereof; wherein $R^1$ is selected from the group consisting of a methyl, an ethyl, a propyl, a carboxyl, a carboxymethyl ester, and a carboxyethyl ester, wherein $R^2$ is selected from the group consisting of a phenyl, a methylphenyl, an ethylphenyl, a propylphenyl, a carboxyphenyl ester, and a carboxyethylphenyl ester; and n is 3, 4, or 5;
   b) a stabilizing effective amount of an excipient composition comprising:
      i) at least one plasticizer present in an amount of about 5% to about 65% by weight of said topical composition,
      ii) at least one antioxidant present in an amount of about 0.02% to about 2.0% by weight of said topical composition,
      iii) at least one gel-forming agent present in an amount of about 0.5% to about 5.0% by weight of said topical composition,
      iv) purified water present in an amount of about 20% to about 80% by weight of said topical composition, and
   c) a pH adjusting agent present in an amount of about 0.2% to about 5.0% by weight of said topical composition to bring said topical composition to a pH from about 5.2 to about 6.6.

2. The composition of claim 1 wherein said active composition comprises 5-methyl-1-phenyl-2-(1H)-pyridone, or a pharmaceutically acceptable salt or ester thereof.

3. The composition of claim 1 wherein said plasticizer comprises a member selected from the group consisting of alkyl glycols, polyalkylene glycols and blends thereof, and said gel-forming agent comprises carboxypolymethylene.

4. The composition of claim 1 wherein said antioxidant comprises sodium metabisulfite.

5. The composition of claim 1 further comprising at least one alcohol.

6. The composition of claim 5 wherein said alcohol is selected from the group consisting of ethanol, isopropanol, and blends thereof.

7. The composition of claim 1 further comprising an emulsifier.

8. The composition of claim 1 further comprising an antimicrobial agent.

9. The composition of claim 8 wherein said antimicrobial agent is selected from the group consisting of methylparaben, propylparaben, and blends thereof.

10. The composition of claim 6 further comprising an antimicrobial agent.

11. The composition of claim 10 wherein said antimicrobial agent is selected from the group consisting of methylparaben, propylparaben, and blends thereof.

12. The composition of claim 10 further comprising an emulsifier.

13. The composition of claim 11 wherein said plasticizer comprises polypropylene glycol.

14. The composition of claim 5 wherein:
a) said active composition is 3% to 7% by weight of said composition,
b) said plasticizer is 5% to 65% by weight of said composition,
c) said antioxidant is 0.02% to 2% by weight of said composition,
d) said gel-forming agent is 0.5% to 5% by weight of said composition,
e) said pH adjusting agent is 0.2% to 5% by weight of said composition,
f) said at least one alcohol is 0% to 20% by weight of said composition, and
g) said purified water is 20% to 80% by weight of said composition.

15. The composition of claim 16 wherein said plasticizer comprises polypropyleneglycol, said antioxidant comprises sodium metabisulfite, said alcohol is selected from the group consisting of ethanol, isopropanol, and blends thereof, and said pH adjusting agent comprises NaOH (5N).

16. The composition of claim 15 further comprising an emulsifier.

17. The composition of claim 15 wherein:
a) said active composition is 3% to 7% by weight of said composition,
said plasticizer is 5% to 65% by weight of said composition,
c) said antioxidant is 0.02% to 2% by weight of said composition,
d) said gel-forming agent is 0.5% to 5% by weight of said composition,
e) said pH adjusting agent is 0.2% to 5% by weight of said composition,
f) said antimicrobial agent is 0% to 0.5% by weight of said composition,
g) said alcohol is 0% to 20% by weight of said composition, and
h) said purified water is 20% to 80% by weight of said composition.

18. A pharmaceutically acceptable topical composition for the treatment and prevention of skin ailments comprising:
a) an active composition present in an amount of about 3% to about 7% by weight of said topical composition comprising 5-methyl-1-phenyl-2-(1H)-pyridone, or a pharmaceutically acceptable salt or ester thereof,
b) a stabilizing effective amount of an excipient composition comprising:
i) at least one plasticizer present in in amount of about 5% to about 65% by weight of said topical composition,
ii) at least one anti-oxidant present in an amount of about 0.02% to about 2.0% a by weight of said topical composition,
iii) at least one gel-forming agent present in an amount of about 0.5% to about 5.0% by weight of said topical composition,
iv) purified water present in an amount of about 200% to about 80% by weight of said topical composition.
v) at least one alcohol present in an amount of 0% to about 20% by weight of said topical composition,
vi) an antimicrobial agent present in an amount of 0% to about 5.0% by weight of said topical composition,
vii) an emulsifier, and
c) a pH adjusting agent present in an amount of about 0.2% to about 5% by weight of said topical composition to bring said topical composition to a pH from about 5.2 to about 6.6.

19. A pharmaceutically acceptable topical composition for the treatment and prevention of skin ailments comprising:
a) an active composition present in an amount of about 3% to about 7% by weight of said topical composition comprising 5-methyl-1-phenyl-2-(1H)-pyridone, or a pharmaceutically acceptable salt or ester thereof,
b) a stabilizing effective amount of an excipient composition comprising:
i) at least one plasticizer present in an amount of about 5% to about 65% by weight of said topical composition,
ii) at least one antioxidant present in an amount of about 0.02% to about 2.0% by weight of said topical composition,
iii) at least one gel-forming agent present in an amount of about 0.5% to about 5.0% of said topical composition,
iv) purified water present in an amount of about 20% to about 80% by weight of said topical composition,
v) at least one alcohol present in amounts of 0% to about 20% by weight of said topical composition,
vi) an antimicrobial agent present in an amount of 0% to about 0.5% by weight of said topical composition,
vii) an emulsifier, and
c) a pH adjusting agent present in an amount of about 0.2% to about 5.0% by weight of said topical composition to bring said topical composition to a pH from about 5.2 to about 6.6, said pH adjusting agent comprising NaOH (5N).

20. The composition of claim 19, wherein said antioxidant comprises sodium bisulfite, said gel-forming agent comprises carboxypolymethylene, said alcohol comprises a member selected from the group consisting of ethanol, isopropanol and blends thereof, and said antimicrobial agent is selected from the group consisting of methylparaben, propylparaben and blends thereof.

* * * * *

UNITED STATES PATENT AND TRADEMARK OFFICE
CERTIFICATE OF CORRECTION

PATENT NO. : 6,492,395 B1  Page 1 of 1
DATED : December 10, 2002
INVENTOR(S) : Scheiwe et al.

It is certified that error appears in the above-identified patent and that said Letters Patent is hereby corrected as shown below:

Title page,
Item [57], ABSTRACT,
Lines 6-7, "...formula: n-(R1)-R2-(1H)pyridone..." should read -- formula: n-(Rl)-1-R2-(1H)pyridone... --.

Column 4,
Line 23, "...warmed to 750°C., and..." should read -- ...warmed to 75°C., and... --.

Column 5,
Line 34, "...stress 41.7/s, at 250°C.)." should read -- -stress 41.7/s, at 25°C.).- --.

Column 7,
Line 18, "...(HPLC) 101,2% of..." should read -- ...(HPLC) 101.2% of... --.
Line 66, "...(HPLC) 99,6% of..." should read --  ...(HPLC) 99.6% of... --.

Column 9,
Line 35, "...said plasticizer is 5%..." should read -- ...b) said plasticizer is 5%... --.

Column 10,
Line 1, "...present in in amount ..." should read -- ...present in an amount... --.
Line 5, "...about 2.0% a by weight ..." should read -- ...about 2.0% by weight ... --.
Line 10, "...amount of about 200%..." should read -- amount of about 20%... --.

Signed and Sealed this

Twenty-eighth Day of October, 2003

JAMES E. ROGAN
*Director of the United States Patent and Trademark Office*